(12) United States Patent
Hwang et al.

(10) Patent No.: US 11,918,988 B2
(45) Date of Patent: Mar. 5, 2024

(54) METHOD FOR PRODUCING CATALYST FOR OXIDATIVE DEHYDROGENATION REACTION, CATALYST FOR OXIDATIVE DEHYDROGENATION REACTION, AND METHOD FOR PRODUCING BUTADIENE USING SAME

(71) Applicant: LG CHEM, LTD., Seoul (KR)

(72) Inventors: Sunhwan Hwang, Daejeon (KR); Jun Kyu Han, Daejeon (KR); San Jin Han, Daejeon (KR); Dong Hyun Ko, Daejeon (KR); Kyoung Yong Cha, Daejeon (KR)

(73) Assignee: LG Chem, Ltd., Seoul (KR)

( * ) Notice: Subject to any disclaimer, the term of this patent is extended or adjusted under 35 U.S.C. 154(b) by 101 days.

(21) Appl. No.: 17/613,486

(22) PCT Filed: Dec. 24, 2020

(86) PCT No.: PCT/KR2020/019103
§ 371 (c)(1),
(2) Date: Nov. 22, 2021

(87) PCT Pub. No.: WO2021/137532
PCT Pub. Date: Jul. 8, 2021

(65) Prior Publication Data
US 2022/0241767 A1  Aug. 4, 2022

(30) Foreign Application Priority Data
Dec. 31, 2019  (KR) .................. 10-2019-0178908

(51) Int. Cl.
*B01J 37/03*   (2006.01)
*B01J 23/80*   (2006.01)
*B01J 37/06*   (2006.01)
*C07C 5/48*    (2006.01)

(52) U.S. Cl.
CPC ............. *B01J 37/038* (2013.01); *B01J 23/80* (2013.01); *B01J 37/06* (2013.01); *C07C 5/48* (2013.01); *C07C 2523/80* (2013.01)

(58) Field of Classification Search
None
See application file for complete search history.

(56) References Cited

U.S. PATENT DOCUMENTS

| | | | |
|---|---|---|---|
| 2007/0032681 | A1 | 2/2007 | Walsdorff et al. |
| 2008/0200741 | A1 | 8/2008 | Kowaleski |
| 2010/0121123 | A1 | 5/2010 | Chung et al. |
| 2010/0280300 | A1 | 11/2010 | Chung et al. |

(Continued)

FOREIGN PATENT DOCUMENTS

| | | |
|---|---|---|
| CN | 102071311 A | 5/2011 |
| CN | 103657659 B | 6/2015 |

(Continued)

OTHER PUBLICATIONS

Liang, CN 208525922U, English Translation from FIT (Year: 2019).*

*Primary Examiner* — Colin W. Slifka
(74) *Attorney, Agent, or Firm* — Bryan Cave Leighton Paisner LLP (57) ABSTRACT

A method for manufacturing a catalyst for oxidative dehydrogenation reaction, a catalyst for oxidative dehydrogenation reaction, and a method for manufacturing butadiene using the same.

8 Claims, 5 Drawing Sheets

(56) References Cited

U.S. PATENT DOCUMENTS

| | | |
|---|---|---|
| 2011/0301022 A1 | 12/2011 | Murakami et al. |
| 2014/0066680 A1 | 3/2014 | Miao et al. |
| 2019/0076836 A1 | 3/2019 | Byun et al. |
| 2019/0299193 A1 | 10/2019 | Han et al. |

FOREIGN PATENT DOCUMENTS

| | | | |
|---|---|---|---|
| CN | 208525922 U | * | 2/2019 |
| CN | 208525922 U | | 2/2019 |
| KR | 10-1999-0014634 A | | 2/1999 |
| KR | 10-0847206 B1 | | 7/2008 |
| KR | 10-0888143 B1 | | 3/2009 |
| KR | 10-2011-0119804 A | | 11/2011 |
| KR | 10-2014-0082869 A | | 7/2014 |
| KR | 10-1902108 B1 | | 9/2018 |
| KR | 10-2018-0122942 A | | 11/2018 |
| KR | 10-1919566 B1 | | 11/2018 |
| KR | 10-2019-0005521 A | | 1/2019 |

* cited by examiner

METHOD FOR PRODUCING CATALYST FOR OXIDATIVE DEHYDROGENATION REACTION, CATALYST FOR OXIDATIVE DEHYDROGENATION REACTION, AND METHOD FOR PRODUCING BUTADIENE USING SAME

CROSS-REFERENCE TO RELATED APPLICATIONS

This application is a U.S. national stage of international Application No. PCT/KR2020/019103 filed Dec. 24, 2020, and claims priority to and the benefit of Korean Patent Application No. 10-2019-0178908 filed in the Korean Intellectual Property Office on Dec. 31, 2019, the entire contents of which are incorporated by reference as if fully set forth herein.

FIELD

The present application relates to a method for manufacturing a catalyst for oxidative dehydrogenation reaction, a catalyst for oxidative dehydrogenation reaction, and a method for manufacturing butadiene using the same.

BACKGROUND 1,3-butadiene is an intermediate of petroleum chemical products, and demands for 1,3-butadiene and the value thereof are gradually increasing globally. 1,3-butadiene has been manufactured using naphtha cracking, the direct dehydrogenation reaction of butene, the oxidative dehydrogenation reaction of butene, and the like.

However, because the naphtha cracking process consumes a lot of energy due to high reaction temperature and is not a process for producing only 1,3-butadiene, a problem associated with the naphtha cracking process is that other fundamental fractions in addition to 1,3-butadiene are produced in excess. Further, the direct dehydrogenation reaction of n-butene is thermodynamically adverse and requires high temperature and low pressure conditions for manufacturing 1,3-butadiene with high yield via an endothermic reaction, and thus is not suitable as a commercialization process for producing 1,3-butadiene.

The oxidative dehydrogenation reaction of butene is a reaction in which butene and oxygen react with each other in the presence of a metal oxide catalyst to produce 1,3-butadiene and water, and has a very thermodynamically favorable advantage because stable water is produced. Further, since the oxidative dehydrogenation reaction of butene is an exothermic reaction unlike the direct dehydrogenation reaction of butene, 1,3-butadiene with high yield can be obtained even at a lower reaction temperature than the direct dehydrogenation reaction. Thus, the oxidative dehydrogenation reaction of butene can become an effective single production process capable of satisfying the demands for 1,3-butadiene because an additional heat supply is not required.

Ferrite-based catalysts are widely known as catalysts for oxidative dehydrogenation reaction of butene. The ferrite-based catalysts are generally synthesized by a co-precipitation method, but it is known that in a catalyst synthesized by the co-precipitation method, a crystal structure active for the oxidative dehydrogenation reaction coexists with an $\alpha\text{-}Fe_2O_3$ crystal structure inactive for the oxidative dehydrogenation reaction. Therefore, a technique for reducing the inactive $\alpha\text{-}Fe_2O_3$ crystal structure during the synthesis of a catalyst or a method for manufacturing a catalyst having excellent activity despite the existence of the inactive crystal structure was required.

In particular, a $ZnFe_2O_4$ catalyst is manufactured by the co-precipitation method using chloride precursors. In a catalyst manufactured by this co-precipitation method, $Cl^-$ remains in the drying step, and $\alpha\text{-}Fe_2O_3$ is present after firing. The remaining $Cl^-$ is discharged in the form of HCl in the firing step, which causes a corrosion problem, and the $\alpha\text{-}Fe_2O_3$ remaining after the firing is responsible for a decrease in the selectivity of 1,3-butadiene.

The amounts of $Cl^-$ and $\alpha\text{-}Fe_2O_3$ need to be adjusted appropriately to manufacture a $ZnFe_2O_4$ catalyst suitable for use in the oxidative dehydrogenation reaction of butene. The amounts of $Cl^-$ and $\alpha\text{-}Fe_2O_3$ can be adjusted by improving the washing efficiency. However, there is a problem in that a large amount of waste water is generated when a washing method of the related art is used.

SUMMARY

The present application has been made in an effort to provide a method for manufacturing a catalyst for oxidative dehydrogenation reaction, a catalyst for oxidative dehydrogenation reaction, and a method for manufacturing butadiene using the same.

An exemplary embodiment of the present application provides a method for manufacturing a catalyst for oxidative dehydrogenation reaction, the method comprising: preparing a catalyst co-precipitation solution; and obtaining a catalyst slurry by washing and filtering the catalyst co-precipitation solution using a filter press comprising a plurality of filter plates, in which the filter plate comprises a stock solution through hole located in the center of the filter plate; and a first quadrant region to a fourth quadrant region positioned around the stock solution through hole, each of the first quadrant region to the fourth quadrant region comprises a through hole through which washing water penetrates, washing water is fed through any one or more of the stock solution through hole and at least one through hole provided in the first quadrant region to the fourth quadrant region, the washing water is discharged through any one or more of the through holes provided in the first quadrant region to the fourth quadrant region, and a discharge rate of the washing water is 5 kg/min or less, and a discharge pressure of the washing water is 0.5 bar to 10 bar.

Further, another exemplary embodiment of the present application provides a catalyst for oxidative dehydrogenation reaction, which is manufactured by the above-described method for manufacturing a catalyst for oxidative dehydrogenation reaction, in which the catalyst is a zinc-ferrite-based catalyst.

Another exemplary embodiment of the present application provides a method for manufacturing butadiene, the method comprising: forming a catalyst layer by filling a reactor with a catalyst for oxidative dehydrogenation reaction, which is manufactured by the above-described manufacturing method; and inducing an oxidative dehydrogenation reaction while continuously passing a reactant comprising a C4 fraction and oxygen through the catalyst layer.

According to the method for manufacturing a catalyst for oxidative dehydrogenation reaction according to an exemplary embodiment of the present application, the washing efficiency is improved by adjusting the discharge rate and the discharge pressure of washing water, so that the amount of waste water generated can be reduced because washing can be performed without using an excessive amount of washing water.

Further, when the method for manufacturing a catalyst for oxidative dehydrogenation reaction according to an exemplary embodiment of the present application is used to manufacture a zinc ferrite-based catalyst, the performance of the manufactured zinc ferrite-based catalyst can be improved by adjusting the amounts of Cl⁻ ions and $\alpha\text{-}Fe_2O_3$ crystals through washing.

DETAILED DESCRIPTION

Hereinafter, the present application will be described in more detail.

In the present application, "water" can be distilled water (DI water).

In the present specification, the "yield (%)" is defined as a value obtained by dividing the number of moles of 1,3-butadiene, which is a product of an oxidative dehydrogenation reaction, by the number of moles of butene which is a raw material. For example, the yield can be represented by the following equation:

Yield (%)=[(the number of moles of 1,3-butadiene produced)/(the number of moles of butene supplied)]×100.

In the present application, the "conversion (%)" refers to a rate at which a reactant is converted into a product. For example, the conversion of butene can be defined by the following equation:

Conversion (%)=[(the number of moles of butene reacted)/(the number of moles of butene supplied)]×100.

In the present specification, the "selectivity (%)" is defined as a value obtained by dividing the change amount of butadiene (BD) by the change amount of butene (BE). For example, the selectivity can be represented by the following equation:

Selectivity (%)=[(the number of moles of 1,3-butadiene or CO$x$ produced)/(the number of moles of butene reacted)]×100.

The conversion and the selectivity of the present application can be measured by a method generally used in the field to which this technology belongs. For example, the conversion and the selectivity can be calculated by gas chromatography (GC) analysis of reactants and products using a GC apparatus. In this case, 6890 or 7890 series manufactured by Agilent Technologies can be used as the GC apparatus.

It is known that the activity of a ferrite-based catalyst having a spinel structure ($AFe_2O_4$) is good as a catalyst for a process of producing 1,3-butadiene through the oxidative dehydrogenation reaction of butene. In this case, A can be a divalent metal, and can be specifically Cu, Ra, Ba, Sr, Ca, Cu, Be, Zn, Mg, Mn, Co, or Ni.

Meanwhile, it is known that a ferrite-based catalyst exhibits a result that is better than that of a bismuth-molybdenum catalyst (Mo—Bi catalyst) in terms of reactivity with 2-butene, particularly, trans-2-butene. Accordingly, even though the Mo—Bi catalyst can be used in the oxidative dehydrogenation reaction of 2-butene, the Mo—Bi catalyst is not as effective at achieving the results, such as the conversion of butene or selectivity of butadiene, as achieved by the catalysts of the present application.

In this case, a $ZnFe_2O_4$ catalyst used in the oxidative dehydrogenation reaction of butene is generally produced by a co-precipitation method. In the co-precipitation method, the $ZnFe_2O_4$ catalyst is manufactured through the processes of precipitating, stirring, aging and washing, drying, and firing, but the problem is that an $\alpha\text{-}Fe_2O_3$ phase is formed in a process of synthesizing a zinc ferrite catalyst using the co-precipitation method of the related art. The $\alpha\text{-}Fe_2O_3$ phase exhibits a low butadiene selectivity in the oxidative dehydrogenation reaction of butene, whereas the $ZnFe_2O_4$ phase exhibits a high butadiene selectivity.

An exemplary embodiment of the present application provides a method for manufacturing a catalyst for oxidative dehydrogenation reaction, the method comprising: preparing a catalytic co-precipitation solution; and obtaining a catalyst slurry by washing and filtering the catalyst co-precipitation solution using a filter press comprising a plurality of filter plates, in which the filter plate comprises a stock solution through hole located in the center of the filter plate; and a first quadrant region to a fourth quadrant region positioned around the stock solution through hole, each of the first quadrant region to the fourth quadrant region comprises a through hole through which washing water penetrates, washing water is introduced through any one or more of the stock solution through hole and at least one through hole provided in the first quadrant region to the fourth quadrant region, the washing water is discharged through any one or more of the through holes provided in the first quadrant region to the fourth quadrant region, and a discharge rate of the washing water is 5 kg/min or less, and a discharge pressure of the washing water is 0.5 bar to 10 bar.

The catalyst co-precipitation solution means a solution containing a catalyst metal precursor precipitate and a metal oxide, which can be formed by an oxidation process. Generally, the catalyst for oxidative dehydrogenation reaction needs to be manufactured as a catalyst slurry by filtering and washing the catalyst metal precursor precipitate, but it is common to use a filter press.

The filter press is configured to comprise a plurality of filter plates, each filter plate comprises a stock solution through hole located in the center of the filter plate and a first quadrant region to a fourth quadrant region positioned around the stock solution through hole, and each of the first quadrant region to the fourth quadrant region comprises a first through hole to a fourth through hole, respectively, through which washing water is discharged.

Figure 1:
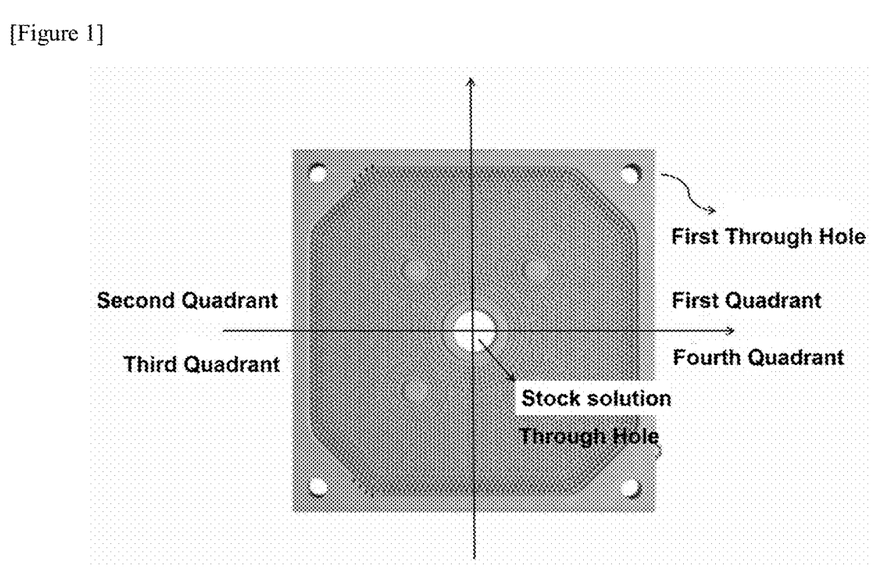
FIG. 1 is a schematic view of a filter plate according to an exemplary embodiment of the present application.

FIG. 1 is a schematic illustration of a filer plate according to an exemplary embodiment of the present application. In an exemplary embodiment of the present application, the first quadrant region can comprise a first through hole, the second quadrant region can comprise a second through hole, the third quadrant region can comprise a third through hole, and the fourth quadrant region can comprise a fourth through hole.

The type and size of the filter press and the filter plate are not particularly limited, but a filter press manufactured by Korea Filter Co., Ltd. can be used, and a membrane plate or recessed plate manufactured by Korea Filter Co., Ltd. can be used as the filter plate.

In an exemplary embodiment of the present application, the catalyst co-precipitation solution can be fed into the stock solution through hole. A precipitate is disposed in the filter plate by feeding the catalyst co-precipitation solution into the stock solution through hole. Thereafter, the precipitate is washed and filtered by feeding or discharging the washing water into the first through hole to the fourth through hole.

In this case, depending on the feed and discharge positions of the washing water, a dead zone which the washing water scarcely reaches is produced in the filter plate, and the washing efficiency is reduced in this dead zone, so that there is a problem in that components requiring washing in a catalyst metal precursor aqueous solution are scarcely washed. For example, when washing water is fed into the first through hole provided at each diagonal position of the filter plate, and the washing water is discharged into the third through hole, or the washing water is fed into the second through hole, and the washing water is discharged into the fourth through hole, there occurs a problem in that the washing water scarcely reaches the dead zone.

The present application is intended to increase the washing efficiency by adjusting the discharge method, discharge rate, discharge pressure, and the like of the washing water to minimize the occurrence of a dead zone inside the filter plate. In the present application, the filter plate was partitioned from the first quadrant region to the fourth quadrant region to indicate a position of the through hole from which the washing water of the filter plate is discharged. Specifically, since the first quadrant region and the third quadrant region are at positions diagonal to each other, the first through hole and the third through hole are present at positions diagonal to each other.

In an exemplary embodiment of the present application, the washing water can be discharged from through holes in quadrant regions adjacent to each other in the first quadrant region to the fourth quadrant region. The through holes in the quadrant region adjacent to each other mean that washing water is discharged through a first through hole in the first quadrant region and a second through hole in the second quadrant region, and do not mean that washing water is discharged through a first through hole in the first quadrant region and a third through hole in the third quadrant region.

For example, when washing water is discharged through the first through hole and the second through hole, the washing water can easily reach the filter plate on the side of the first through hole while being discharged through the first through hole, and the washing water can easily reach the filter plate on the side of the second through hole while being discharged through the second through hole. In this case, the washing water can easily reach the dead zone located between the first through hole and the second through hole to increase the washing efficiency.

In an exemplary embodiment of the present application, the first quadrant region can comprise a first through hole, the second quadrant region can comprise a second through hole, the third quadrant region can comprise a third through hole, the fourth quadrant region can comprise a fourth through hole, washing water can be fed through the stock solution through hole, and the washing water can be simultaneously discharged through all of the first through hole to the fourth through hole.

In an exemplary embodiment of the present application, the first quadrant region can comprise a first through hole, the second quadrant region can comprise a second through hole, the third quadrant region can comprise a third through hole, the fourth quadrant region can comprise a fourth through hole, washing water can be fed into the first through hole or the second through hole, and the washing water can be discharged through the first through hole or the fourth through hole.

In the present application, washing water can be allowed to easily reach the dead zone inside the filter plate by adjusting the feed or discharge flow rate of washing water discharged in addition to adjusting the position where the washing water is discharged to increase the time for the washing water to stay inside the filter plate.

Specifically, the through holes from which the washing water is discharged are connected to each other by a washing water discharge hose, and a flow rate adjusting valve is provided at the rear end of the washing water discharge hose, and the flow rate of washing water can be adjusted using the flow rate adjusting valve. Further, in addition to the flow rate adjusting valve, a pressure gauge can be additionally provided at a rear end of the washing water discharge hose.

In addition, the washing water can be discharged sequentially or simultaneously through the respective through holes, but when the washing water is simultaneously discharged, the pressure is maintained at the same level by the washing water discharged from the respective through holes, so that the washing water can uniformly reach the inside of the filter plate. Furthermore, the discharge flow rate can be adjusted by the flow rate adjusting valve located at the rear end of the washing water discharge hose, so that the washing water can reach the back side of the filter plate.

Through this, there is an advantage in that a uniform washing efficiency can be obtained regardless of the position of the filter plate.

The deviation of the discharge rate of the washing water discharged by each of the through holes can be adjusted within 10%, 5%, or 1%.

The washing water can be fed into a stock solution through hole in addition to the above-described first through hole to the fourth through hole. In this case, after the catalyst co-precipitation solution is fed into the stock solution through hole, and a certain period of time has passed, then the washing water can be fed into the stock solution through hole.

The feed rate of the washing water can be 1 kg/min to 20 kg/min, preferably 2 kg/min to 15 kg/min, and more preferably 3 kg/min to 10 kg/min. When the feed rate satisfies the above numerical range, the washing water can easily reach the filter plate, and it is possible to prevent the pressure inside the filer plate from increasing excessively. Through this, the washing efficiency can be increased.

The discharge rate and discharge pressure of the washing water of the present application can be adjusted to increase the time for the washing water to stay in the filter plate. For the adjustment, a flow rate adjusting valve installed in the above-described washing water discharge hose can be used, and the discharge pressure can be confirmed by checking the pressure gauge with the unaided eye. As the flow rate adjusting valve, a general valve made of a plastic or metal material can be used.

Specifically, a discharge rate of the washing water can be 5 kg/min or less, and a discharge pressure of the washing water can be 0.5 bar to 10 bar. Further, the discharge rate of the washing water can be 4.9 kg/min or less, the discharge pressure of the washing water can be 0.5 bar to 8 bar, and preferably, the discharge rate of the washing water can be 4.8 kg/min or less, and the discharge pressure of the washing water can be 1 bar to 5 bar. When the above ranges are satisfied, the washing water is discharged so quickly that a sufficient washing effect cannot be expected. However, when the above ranges are satisfied, the washing water can easily reach the dead zone because the time for the washing water to stay inside the filter plate increases, so that a high washing efficiency can be expected even with a small amount of washing water. The discharge rate of the washing water can be calculated by measuring the weight of the washing water discharged at regular time (5 minutes) intervals.

In the present application, the discharge rate of the washing water is based on the total amount of the washing water discharged through the through holes.

The difference between the feed pressure of the washing water and the discharge pressure of the washing water can be adjusted to 5 bar or less, preferably 4 bar or less, and more preferably 3 bar or less. In this case, the washing water can be stably fed and discharged, and can stably reach the dead zone inside the filter plate.

Hereinafter, steps other than the preparation of the catalyst slurry will be described.

Preparation of the catalyst co-precipitation solution can comprise: preparing a catalyst precursor aqueous solution; and co-precipitating a catalyst component by adding the catalyst precursor aqueous solution and a basic aqueous solution to a co-precipitation bath.

The catalyst precursor aqueous solution means an aqueous solution containing precursor components of a catalyst component. For example, when a target catalyst is a zinc-ferrite-based catalyst, the catalyst precursor aqueous solution contains zinc precursor and iron precursor components.

The zinc precursor and the iron precursor can be each independently one or more selected from the group consisting of a nitrate, an ammonium salt, a sulfate, and a chloride. Among them, as the precursors are inexpensive and easily purchased, preferably, the precursors can be selected from a nitrate and a chloride in consideration of a catalyst manufacturing cost for mass production.

The zinc precursor can be a divalent zinc precursor, and can be specifically zinc chloride ($ZnCl_2$). In this case, a zinc ferrite catalyst is easily formed.

The iron precursor can be a trivalent iron precursor, and can be specifically ferric chloride hydrate ($FeCl_3.6H_2O$). In this case, the formation of the zinc ferrite catalyst is excellent.

The zinc precursor and the iron precursor are mixed with water to prepare a metal precursor aqueous solution. When the metal precursor is dissolved in water and is present in a liquid state, ions of zinc and iron are easily exchanged, so that a target co-precipitate can be easily prepared.

The mixing ratio (molar ratio) of the zinc precursor and the iron precursor in the metal precursor aqueous solution can be 1:1.5 to 1:10, preferably 1:2 to 1:5, and more preferably 1:2 to 1:3. Within the above ranges, a crystal structure active for the oxidative dehydrogenation reaction is easily formed, so that there is an effect of having excellent catalyst activity.

The metal precursor aqueous solution can be an acidic solution, and the exemplary pH thereof can be 0 to 4, 1 to 3, or 1 to 2, and there is an effect in that a target active component is stably formed within this range.

The step of co-precipitating a catalyst includes adding the catalyst precursor aqueous solution and a basic aqueous solution to a co-precipitation bath.

The basic aqueous solution can be one selected from the group consisting of potassium hydroxide, ammonium carbonate, ammonium hydrogen carbonate, a sodium hydroxide aqueous solution, a sodium carbonate aqueous solution, and ammonia water, or a mixed solution thereof. Preferably, the basic aqueous solution can be ammonia water.

A concentration of the basic aqueous solution can be 5 wt % to 20 wt % based on the weight of the entire aqueous solution in the co-precipitation bath. Preferably, the concentration can be 5 wt % to 10 wt %.

The pH of the co-precipitation bath can be adjusted to 6 or higher, preferably 6 to 10, and more preferably 7 to 8 by first feeding the basic aqueous solution into the co-precipitation bath before adding the metal precursor aqueous solution to the co-precipitation bath. In this case, the feeding of the metal precursor aqueous solution prevents the pH from being changed excessively immediately after the feeding, so that the catalyst can be stably co-precipitated.

As an example, the basic aqueous solution and the metal precursor aqueous solution can be instilled from separate exhaust nozzles, and in this case, the amount of basic aqueous solution supplied can be easily adjusted.

The co-precipitation bath can be filled with water, and the temperature of the co-precipitation bath can be, for example, 20° C. to 30° C., 22° C. to 25° C., or room temperature.

After the co-precipitating of the catalyst component, a step of stirring the solution or aging the solution can be further performed, and in this case, there is an effect in which the reaction is sufficiently performed in the solution.

As an example, the stirring is not particularly limited as long as it is a stirring method typically used in the art, but as an example, the stirring can be performed for 30 minutes to 3 hours, 30 minutes to 2 hours, or 30 minutes to 1 hour and 30 minutes using a stirring stirrer.

The aging can be performed, for example, for 30 minutes to 3 hours, 30 minutes to 2 hours, or 30 minutes to 1 hour and 30 minutes.

The drying of the catalyst slurry and the firing of the catalyst slurry can be further performed. Through the drying and firing step, it is possible to form a metal-oxide catalyst in the form in which the catalyst metal component present in the catalyst slurry is precipitated.

For example, the drying can be performed at 60° C. to 100° C., 70° C. to 100° C., or 80° C. to 100° for 12 hours to 20 hours, 14 hours to 20 hours, or 14 hours to 18 hours using a typical dryer.

The firing can be maintained between 600° C. to 800° C. for 5 hours to 10 hours by increasing the temperature at a rate of 1° C./min at 80° C. In the firing of the catalyst slurry, the catalyst slurry can be fired specifically at 600° C. to 700° C., and more specifically at 600° C. to 650° C. The catalyst slurry can be fired specifically for 5 hours to 8 hours, more specifically 5 hours to 6 hours.

The crystal size of the $ZnFe_2O_4$ structure of the catalyst is controlled by the above temperature range, and the crystal size tends to increase as the temperature increases. In the dehydrogenation reaction of the present application, the adsorption and desorption of oxygen are very important, and the higher the crystallinity, the lower the amount of desorbed oxygen, so that the reactivity can be decreased. For example, a commercially available $ZnFe_2O_4$ exhibits very good crystallinity, but the activity is very low in the present reaction. For this reason, it is very important to produce a catalyst having appropriate crystallinity, and the firing temperature is essential for the catalyst.

It is generally known that the above time range has a tendency similar to temperature, but adjusting of the time range can be less effective than increasing the temperature, and if the time is too long, the production time is too long when several tons of catalyst is later produced during commercialization, so that the firing time is generally adjusted to 6 hours or so in the laboratory setting.

When the temperature and the time are outside the above temperature and time ranges, for example, if the temperature is less than 600° C., crystals are weakly formed, so that the structural stability deteriorates. In contrast, when the temperature is more than 800° C., the crystallinity is so high that a less active catalyst can be produced. In conclusion, appropriate crystallinity is important in consideration of catalyst characteristics and reaction characteristics of the feed, and these can be controlled by controlling the temperature and time in the firing of the second precipitate.

In the present application, the catalyst for oxidative dehydrogenation reaction is a catalyst manufactured by the method for manufacturing a catalyst for oxidative dehydrogenation reaction, and can be a zinc-ferrite-based catalyst.

The zinc ferrite catalyst can comprise a $ZnFe_2O_4$ crystal structure.

Further, the zinc ferrite catalyst can be a mixed phase of the $ZnFe_2O_4$ crystal structure and $\alpha\text{-}Fe_2O_3$.

The presence/content ratio of the $ZnFe_2O_4$ crystal structure and the $\alpha\text{-}Fe_2O_3$ crystal structure of the zinc ferrite catalyst can be calculated from the area ratio of the peak corresponding to each phase of the XRD analysis.

The diffraction peaks corresponding to the $ZnFe_2O_4$ crystal structure are present at positions (220), (311), (400), (422), (511), and (440), and the diffraction peaks corresponding to the $\alpha\text{-}Fe_2O_3$ are present at the position (104).

The content of the crystal structure of $\alpha\text{-}Fe_2O_3$ of the zinc ferrite catalyst can be 18 parts by weight or less, preferably 13 parts by weight or less based on 100 parts by weight of the entire $ZnFe_2O_4$ crystal structure and $\alpha\text{-}Fe_2O_3$ crystal structure. When the above range is satisfied, the proportion of the crystal structure of $\alpha\text{-}Fe_2O_3$ is reduced, which results in an increase in the activity of the catalyst. Meanwhile, the lower limit value of the content of the crystal structure of $\alpha\text{-}Fe_2O_3$ is not particularly limited, but can be 1 part by weight or more, preferably 2 parts by weight or more, and more preferably 3 parts by weight or more, based on 100 parts of the entire $ZnFe_2O_4$ crystal structure and $\alpha\text{-}Fe_2O_3$ crystal structure.

The zinc ferrite catalyst manufactured by the manufacturing method of the present application can be used for a method for manufacturing butadiene by an oxidative dehydrogenation reaction of butene.

The zinc ferrite catalyst manufactured by the above-described manufacturing method can have a molar ratio of ferrite to zinc (ferrite/zinc (Fe/Zn$^a$)) of 1 to 2.5. Preferably, the molar ratio can be 2 to 2.5. More preferably, the molar ratio can be 2 to 2.4. When the molar ratio of ferrite to zinc is within the above range, the molar ratio is helpful in increasing the crystal structure and activity of the zinc ferrite catalyst and the zinc ferrite phase is excellently formed by adjusting the $\alpha\text{-}Fe_2O_3$ phase within a certain range, so that there is an effect in that the selectivity and yield of butadiene according to the oxidative dehydrogenation reaction are excellent. The molar ratio (ferrite/zinc (Fe/Zn$^a$)) of ferrite to zinc is a value measured to see to what degree the ratio of Fe/Zn on the surface of an actual catalyst measured through an energy dispersive X-ray spectrometer (EDS) characteristic analysis is dispersed. The a of Zn$^a$ indicates the oxidation state of zinc, and can be +2.

The oxidative dehydrogenation reaction of butene of the present application can be named as a method for manufacturing butadiene. The method for manufacturing butadiene can comprise performing an oxidative dehydrogenation reaction while passing a reactant containing a C4 fraction and oxygen through a reactor filled with a zinc ferrite catalyst manufactured by the above-described manufacturing method.

The method for manufacturing butadiene comprises: forming a catalyst layer by filling a reactor with a catalyst for oxidative dehydrogenation reaction manufactured by the above-described manufacturing method; and inducing an oxidative dehydrogenation reaction while continuously passing a reactant containing a C4 fraction and oxygen through the catalyst layer.

The C4 fractions can mean C4 raffinate-1,2,3 remaining by separating useful compounds from a C4 mixture produced by naphtha cracking, and can mean C4 classes which can be obtained through ethylene dimerization. Specifically, the C4 fraction can be one or a mixture of two or more selected from the group consisting of n-butane, trans-2-butene, cis-2-butene, and 1-butene.

The reactant can contain steam or nitrogen ($N_2$) in addition to a C4 fraction and oxygen. The steam or nitrogen ($N_2$) is a diluted gas introduced for the purpose of reducing the explosion danger of the reactant, preventing coking of the catalyst, removing the reaction heat, and the like.

The oxygen ($O_2$) is an oxidant and reacts with C4 fractions to cause a dehydrogenation reaction.

The oxidative dehydrogenation reaction can proceed by the following Reaction Scheme 1 or Reaction Scheme 2:

$C_4H_8 + \frac{1}{2}O_2 \rightarrow C_4H_6 + H_2O$  [Reaction Scheme 1]

$C_4H_{10} + O_2 \rightarrow C_4H_6 + 2H_2O.$  [Reaction Scheme 2]

Hydrogen of butane or butene is removed by the oxidative dehydrogenation reaction, and as a result, butadiene is produced. Meanwhile, the oxidative dehydrogenation reaction can produce a side reaction product comprising carbon monoxide (CO), carbon dioxide ($CO_2$), or the like, in addition to the main reaction such as Reaction Scheme 1 or 2. The oxidative dehydrogenation reaction can comprise a process in which the side reaction product is separated so as not to be continuously accumulated in the process, and is released out of the system.

In the method for manufacturing butadiene, the conversion of butene can be 72% or more, preferably 72.5% or more, and more preferably 79% or more.

In the method for manufacturing butadiene, the selectivity of butadiene can be 85% or more, preferably 85.8% or more, and more preferably 87% or more.

The oxidative dehydrogenation reaction can be performed under the conditions of a gas hourly space velocity (GHSV) of 100 h$^{-1}$ to 400 h$^{-1}$ at a reaction temperature of 200° C. to 600° C., and a pressure of 0.1 bar to 10 bar.

Hereinafter, the present specification will be described in detail with reference to Examples for specifically describing the present specification. However, the Examples according to the present specification can be modified in various forms, and it is not interpreted that the scope of the present specification is limited to the Examples described below in detail. The Examples of the present specification are provided to explain the present specification more completely to a person with ordinary skill in the art.

EXAMPLES

Example 1

1) Preparation of Catalyst Co-Precipitation Solution

A metal precursor aqueous solution was prepared by dissolving 0.122 mol of zinc chloride ($ZnCl_2$) and 0.243 mol of ferric chloride ($FeCl_3 \cdot H_2O$) in 12.778 mol of water. In this case, the molar ratio of the metal components comprised in the metal precursor aqueous solution was Fe:Zn=2:1.

Next, a process of co-precipitating iron and zinc was performed by instilling the metal precursor aqueous solution together with ammonia water having a concentration of 10 wt % into a co-precipitation tank (pH 7 to 9) in which ammonia water was prepared. The process of stirring the co-precipitation solution for 1 hour was performed such that the co-precipitation was sufficiently performed, and then the stirring was interrupted and the co-precipitate was aged by allowing the precipitates to stand at room temperature for 1 hour such that all the precipitates would settle.

2) Obtaining of Catalyst Slurry

A catalyst slurry was obtained by feeding the prepared catalyst co-precipitation solution into a filter press equipped with a filter plate for filtration and washing.

Figure 2:
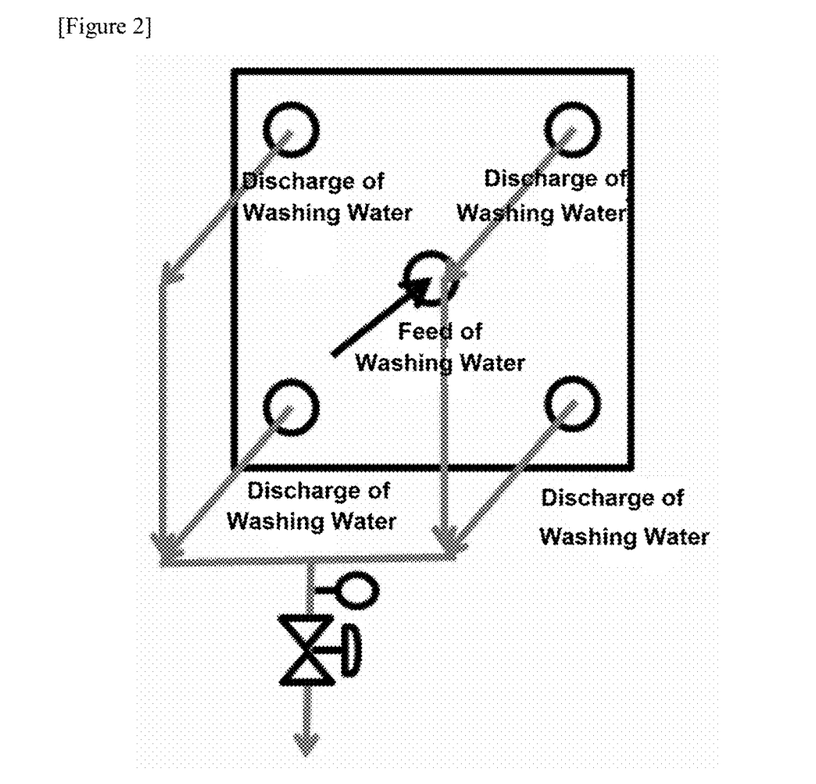
FIGS. 2 to 4 are schematic views illustrating the discharge of washing water from the filter plates in the Examples and the Comparative Examples of the present application.

The filter plate included a stock solution through hole located in the center of the filter plate; and a first quadrant region to a fourth quadrant region partitioned around the stock solution through hole, and each of the first quadrant region to the fourth quadrant region include a first through hole to a fourth through hole through which washing water penetrates, as illustrated in FIGS. 1 and 2.

In this case, the catalyst co-precipitation solution was fed into the stock solution through hole, and the washing water was additionally fed into the stock solution through hole (feed amount: 1,260 kg, feed rate: 5.2 kg/min, feed pressure: 3 bar).

The through holes through which the washing water was discharged were connected to each other by a washing water discharge hose, and a flow rate adjusting valve and a pressure gauge were provided at the rear end of the discharge hose, and the discharge rate and discharge pressure of the washing water were adjusted by this valve, and as a result, the washing water was uniformly fed into the entire filter plate and the washing water was allowed to stay inside the filter plate for a long time.

The washing water discharged from each of the first through hole to the fourth through hole was discharged at the same discharge rate, the total discharge rate was 4.1 kg/min, and the discharge pressure was adjusted to 1 bar.

The washing water was discharged through all of the first through hole to the fourth through hole as illustrated in FIG. 2.

The feed rate of the washing water was determined by measuring the weight of the washing water fed at certain time (5 minutes) intervals, and the discharge rate of the washing water was determined by measuring the weight of the washing water discharged at certain time (5 minutes) intervals.

In this case, a 800 mm filter press manufactured by Korea Filter Co., Ltd. was used as the filter press, and an 800 mm membrane plate or a 800 mm recessed plate manufactured by Korea Filter Co., Ltd. was used as the filter plate.

3) Preparation of Catalyst

After all washing and filtration was completed, a catalyst slurry cake was separated from the filter plate. Thereafter, the slurry cake was placed in a separate tray and dried at 90° C. for 24 hours, and then the dried co-precipitate was placed in a firing furnace to increase the temperature up to 650° C. at a rate of 1° C./min. The temperature was then maintained at 650° C. for 6 hours, after which it was cooled to 20° C., thereby manufacturing a zinc ferrite catalyst.

Comparative Example 1

Figure 3:
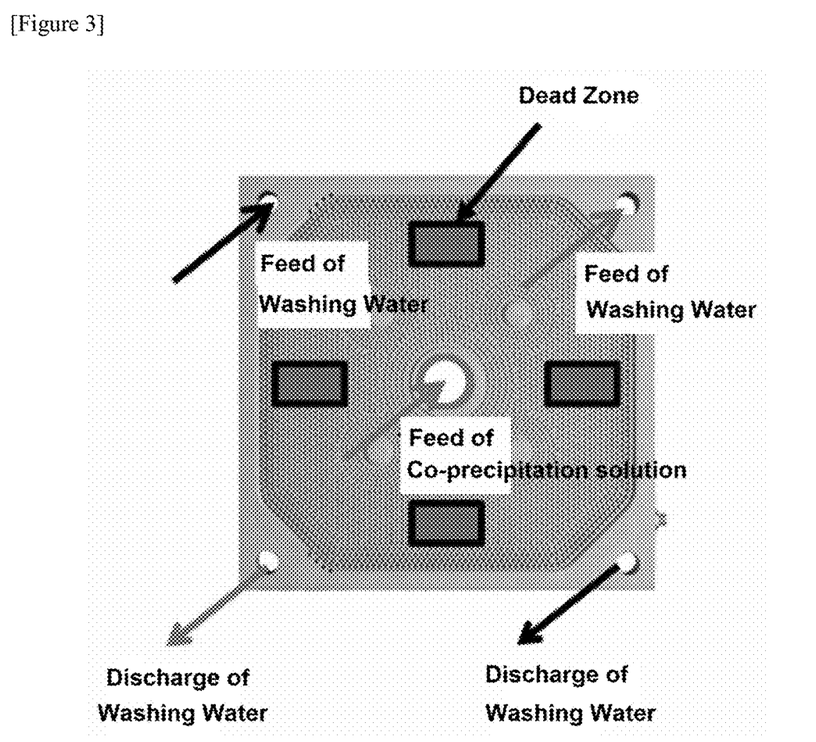

As illustrated in FIG. 3, the washing water was fed into the first through hole, and the washing water was discharged through the third through hole. Thereafter, the washing water was fed into the second through hole, and the washing water was discharged through the fourth through hole. The through holes through which the washing water was discharged were connected to each other by a washing water discharge hose, but the flow rate of the discharged washing water was not adjusted because a separate flow rate adjusting valve was not used. A zinc ferrite catalyst was manufactured in the same manner as in Example 1 except for the above content.

The amount of the washing water fed into the first through hole and the second through hole was each 630 kg, the total feed rate of the washing water was 5.2 kg/min, the discharge rate of the washing water is 5.2 kg/min, and the discharge pressure of the washing water was 0 bar.

Example 2

As shown in Table 1 below, Example 2 was performed in the same manner as in Example 1, except that each of the feed rate, discharge rate, feed pressure, and discharge pressure of the washing water was adjusted.

Comparative Example 2

As shown in Table 1 below, Comparative Example 2 was performed in the same manner as in Example 1, except that the feed rate, discharge rate, feed pressure, and discharge pressure of the washing water were adjusted.

Example 3

Figure 4:
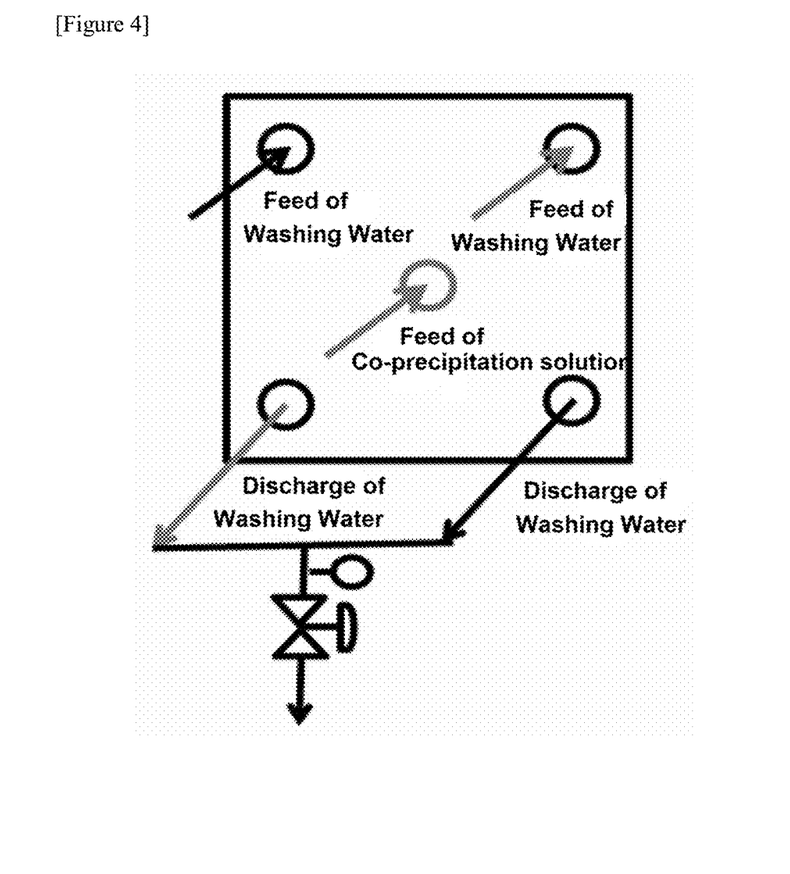

A zinc ferrite catalyst was manufactured in the same manner as in Comparative Example 1, except that the through holes through which the washing water was discharged were connected to each other by a washing water discharge hose, and a flow rate adjusting valve and a pressure gauge were provided at the rear end of the discharge hose, and the feed rate, discharge rate, and discharge pressure of the washing water were adjusted by this valve. That is, the washing water was discharged by the method illustrated in FIG. 4.

The amount of the washing water fed into the first through hole and the second through hole was each 630 kg, the total feed rate of the washing water was 5.2 kg/min, the discharge rate of the washing water was 4.1 kg/min, and the discharge pressure of the washing water was 1 bar.

TABLE 1

|  | Washing water | | | | |
| --- | --- | --- | --- | --- | --- |
|  | Total feed amount (kg) | Feed rate (kg/min) | Feed pressure (bar) | Discharge rate (kg/min) | Discharge pressure (bar) |
| Example 1 | 1,260 | 5.2 | 3 | 4.1 | 1 |
| Example 2 | 1,260 | 6 | 4 | 4.8 | 1 |
| Example 3 | 1,260 | 5.2 | 3 | 4.1 | 1 |
| Comparative Example 1 | 1,260 | 5.2 | 2.5 | 5.2 | 0 |
| Comparative Example 2 | 1,260 | 7.1 | 4 | 5.2 | 0.5 |

Experimental Example 1

The $Cl^-$ ion content was analyzed using a combustion ion chromatography (IC) apparatus.

In addition, to compare the formation ratios of $ZnFe_2O_4$ and $\alpha\text{-}Fe_2O_3$, an X-Ray diffraction (XRD) analysis of the zinc ferrite catalysts manufactured in the above Comparative Examples and Examples was performed.

In this case, the measurement was performed in a range of 20 to 80 degrees based on 2theta, and a Cu target was used.

The ratio of the area of the peaks (positions (220), (311), (222), (400), (422), (511), (440) position) corresponding to $ZnFe_2O_4$ to the area of the peak (position: 104) corresponding to $\alpha\text{-}Fe_2O_3$ corresponds to the weight ratio of each phase.

Specifically, after registering the peaks of $ZnFe_2O_4$ and $\alpha\text{-}Fe_2O_3$ by TOPAS, which is a program in the Bruker XRD device, the area ratio of peaks was calculated based on each main peak by the method calculated through simulation.

Figure 5:
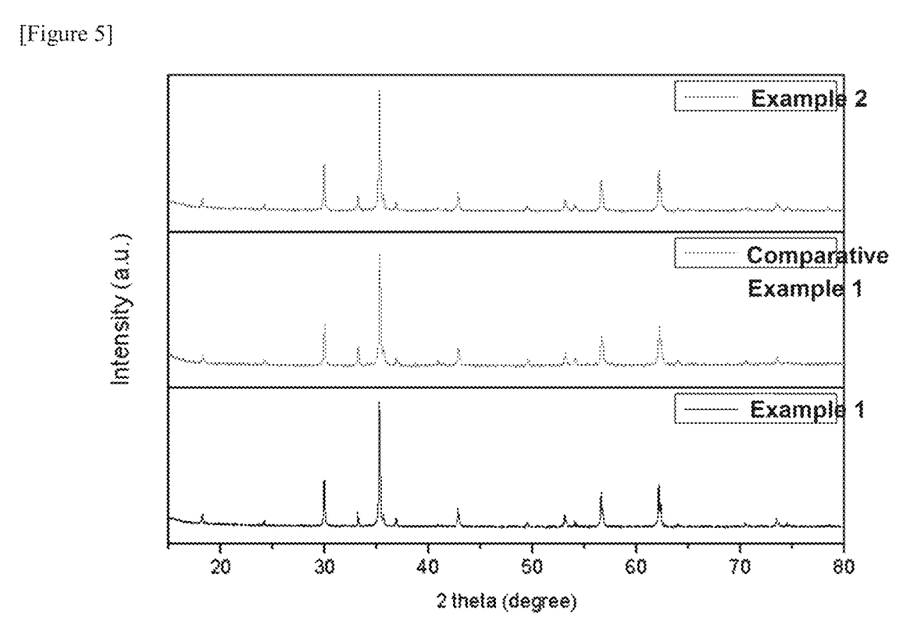
FIG. 5 is a plot showing the X-ray diffraction data of the zinc ferrite catalysts of Experimental Example 1 of the present application.

An XRD analysis of the Comparative Examples and the Examples is shown in FIG. 5.

TABLE 2

|  | $Cl^-$ content (wt %) | $ZnFe_2O_4$ content (wt %) | $\alpha\text{-}Fe_2O_3$ content (wt %) |
|---|---|---|---|
| Example 1 | 2.5 | 87.3 | 12.7 |
| Example 2 | 5.4 | 84.99 | 15.01 |
| Example 3 | 5.7 | 82.2 | 17.8 |
| Comparative Example 1 | 7.6 | 81.6 | 18.4 |
| Comparative Example 2 | 9.3 | 80.5 | 19.5 |

As shown in the results, in Comparative Examples 1 and 2, the discharge rate and the discharge pressure of the discharged washing water were not adjusted to specific ranges, and the washing water did not sufficiently stay in the filter plate, so that the washing water scarcely reached the dead zone of the filter plate. For this reason, it could be confirmed that the chlorine ions were not sufficiently washed, and as a result, the performance of the catalyst deteriorated.

In Examples 1 to 3 according to exemplary embodiments of the present application, chlorine ions could be effectively washed by adjusting the discharge rate and discharge pressure of the washing water to specific ranges, compared to the Comparative Examples, and accordingly, as described below, it could be confirmed that the performances of the catalysts manufactured according to Examples 1 to 3 were improved compared to those of the Comparative Examples.

Experimental Example 2

Under the conditions of GHSV=66.5 $h^{-1}$, OBR=1, SBR=8, and NBR=1, 1,3-butadiene was manufactured from the oxidative dehydrogenation reaction by using the zinc ferrite catalysts prepared in the Examples and the Comparative Examples. A metal tubular fixed bed reactor was used as the reactor. The fixed bed reactor was filled with 200 cc of each of the catalysts prepared in the Examples and the Comparative Examples and infused with water. The water was vaporized into steam at 120° C. using a vaporizer, the steam was mixed with the butene mixture and oxygen as the reactants, and the resulting mixture was allowed to flow into the reactor.

OBR=Oxygen/total 2-butene ratio
SBR=Steam/total 2-butene ratio
NBR=Nitrogen/total 2-butene ratio In this case, the conversion, yield, and selectivity of the reactants and products were calculated using gas chromatography (GC).

<GC Analysis Conditions>
1) Column: HP-1(100 m×350 μm×0.5 μm)
2) Injection volume: 1 μl
3) Inlet Temp.: 280° C., Pressure: 36.2 psi, Total flow: 33.5 ml/min, Split flow: 60 ml/min, spilt ratio: 10:1
4) Column flow: 1.42 ml/min
5) Oven temp.: 50° C./15 min-10° C./min-260° C./18 min (Total 52 min)
6) Detector temp.: 280° C., $H_2$: 35 ml/min, Air: 300 ml/min, He: 20 ml/min
7) GC Model: Agilent 6890

TABLE 3

|  | Butene Conversion (%) | Butadiene Selectivity (%) | Butadiene Yield (%) | COx Selectivity (%) |
|---|---|---|---|---|
| Example 1 | 87.4 | 87.8 | 76.8 | 11.1 |
| Example 2 | 86.1 | 87.3 | 75.2 | 11.7 |
| Example 3 | 85.9 | 87.1 | 74.8 | 11.8 |
| Comparative Example 1 | 81.6 | 86.1 | 70.3 | 14.0 |
| Comparative Example 2 | 77.4 | 84.6 | 65.5 | 14.3 |

As shown in the results, according to the method for manufacturing a catalyst for oxidative dehydrogenation reaction according to an exemplary embodiment of the present application, the washing efficiency is improved by adjusting the discharge rate and the discharge pressure of washing water, so that the amount of waste water generated can be reduced because washing can be performed without using an excessive amount of washing water.

Further, when the method for manufacturing a catalyst for oxidative dehydrogenation reaction according to an exemplary embodiment of the present application is used to manufacture a zinc ferrite-based catalyst, the performance of the manufactured zinc ferrite-based catalyst can be improved by adjusting the amounts of $Cl^-$ ions and $\alpha\text{-}Fe_2O_3$ crystals through washing.

In particular, in Example 1, the washing water is discharged through all of the first through hole to the fourth through hole, and the discharge rate and the discharge pressure of the washing water are adjusted under specific conditions. In this case, it can be confirmed that chlorine ions are washed more effectively than when the washing water is not discharged through all of the first through hole to the fourth through hole, or when the discharge rate and discharge pressure of the washing water are not adjusted under specific conditions, and it can be confirmed that the performance of the manufactured catalyst is the best.

The invention claimed is:

1. A method for manufacturing a catalyst for oxidative dehydrogenation reaction, the method comprising:
    preparing a catalyst co-precipitation solution containing a zinc precursor and an iron precursor, wherein the zinc precursor and the iron precursor are each independently one or more selected from the group consisting of a nitrate, an ammonium salt, a sulfate, and a chloride; and
    obtaining a catalyst slurry by washing and filtering the catalyst co-precipitation solution using a filter press comprising a plurality of filter plates,
    wherein each of the plurality of filter plates comprises a stock solution through hole located at a center of the filter plate, and a first quadrant region to a fourth quadrant region arranged around the stock solution through hole, wherein each of the first quadrant region to the fourth quadrant region comprises a washing water through hole, wherein the washing water is fed through one or more of the stock solution through hole and at least one of the washing water through holes, wherein the washing water is discharged through one or more of the washing water through holes, wherein a discharge rate of the washing water is 5 kg/min or less, and a discharge pressure of the washing water is 0.5 bar to 10 bar, and wherein the catalyst is a zinc-ferrite-based catalyst.

2. The method of claim 1, wherein the catalyst co-precipitation solution is fed into the stock solution through hole.

3. The method of claim 1, wherein the washing water is fed through the stock solution through hole, and wherein the washing water is simultaneously discharged through all of the washing water through holes.

4. The method of claim 1, wherein the first quadrant region comprises a first washing water through hole, the second quadrant region comprises a second washing water through hole, the third quadrant region comprises a third washing water through hole, and the fourth quadrant region comprises a fourth washing water through hole, wherein the washing water is fed through the first washing water through hole or the second washing water through hole, and wherein the washing water is discharged through the third washing water through hole or the fourth washing water through hole.

5. The method of claim 1, wherein the washing water through holes through which the washing water is discharged are connected to each other by a washing water discharge hose, and wherein a flow rate adjusting valve and a pressure gauge are provided at a rear end of the washing water discharge hose.

6. The method of claim 1, wherein a feed rate of the washing water is 1 kg/min to 20 kg/min.

7. The method of claim 1, wherein the preparing of the catalyst co-precipitation solution comprises:

preparing a catalyst precursor aqueous solution; and co-precipitating a catalyst component by adding the catalyst precursor aqueous solution and a basic aqueous solution to a co-precipitation bath.

8. The method of claim 1, further comprising drying the catalyst slurry and firing the catalyst slurry.

* * * * *